United States Patent [19]

Moldt

[11] Patent Number: 5,097,063

[45] Date of Patent: Mar. 17, 1992

[54] HYDROXYCARBONYL DERIVATIVES AND PROCESS FOR MAKING THE SAME

[75] Inventor: Peter Moldt, Humlebæk, Denmark

[73] Assignee: NeuroSearch A/S, Glostrup, Denmark

[21] Appl. No.: 632,489

[22] Filed: Dec. 24, 1990

Related U.S. Application Data

[63] Continuation-in-part of Ser. No. 473,352, Feb. 1, 1990, abandoned.

[30] Foreign Application Priority Data

Nov. 27, 1989 [DK] Denmark ............................. 5954/89

[51] Int. Cl.⁵ ..................... C07C 331/01; C07C 45/00
[52] U.S. Cl. ................................... 560/303; 568/347; 568/351; 568/352
[58] Field of Search ................. 568/347, 351, 352; 560/303

[56] References Cited

U.S. PATENT DOCUMENTS

| | | | |
|---|---|---|---|
| 3,311,656 | 3/1967 | Sarmatis | 568/347 |
| 3,904,586 | 9/1975 | Derible et al. | 560/303 |
| 4,088,689 | 5/1978 | Rosenberger | 588/11 |
| 4,105,855 | 8/1978 | Schulz et al. | 560/202 |
| 4,156,190 | 5/1979 | Kienzle | 560/61 |
| 4,204,073 | 5/1980 | Kienzle | 560/231 |
| 4,212,827 | 7/1980 | Paust et al. | 568/348 |
| 4,245,109 | 1/1981 | Mayer et al. | 560/61 |
| 4,283,559 | 8/1981 | Broger et al. | 568/11 |
| 4,585,885 | 4/1986 | Bernard et al. | 556/444 |
| 4,883,887 | 11/1989 | Bernard et al. | 560/11 |

Primary Examiner—C. Warren Ivy
Assistant Examiner—Raymond Covington
Attorney, Agent, or Firm—Gordon W. Hueschen

[57] ABSTRACT

The present invention relates to a process for the preparation of astaxanthin having the formula

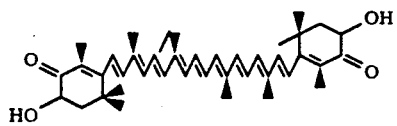

comprising the step of oxidizing a dienolether, a dienamine, or a dienolate anion of canthaxanthin with an oxaziridine oxidant to produce an astaxanthin dihemiaminal, and then decomposing the dihemiaminal to produce astaxanthin. The process advantageously involves two less steps than the best known prior art process for the preparation of astaxanthin.

The invention also relates to important intermediates in the preparation of astaxanthin, which is itself an important additive in the fish industry, the most important of which intermediates is the astaxanthin dihemiaminal.

25 Claims, No Drawings

HYDROXYCARBONYL DERIVATIVES AND PROCESS FOR MAKING THE SAME

This is a continuation-in-part of Ser. No. 473,352 filed Feb. 1, 1990, now abandoned.

FIELD OF INVENTION

The present invention relates to a novel process for the manufacture of hydroxycyclohexenone derivatives, more specifically to the manufacture of astaxanthin and to intermediates therefor. Astaxanthin is widely used and has important value as an additive in the fish industry.

BACKGROUND OF THE INVENTION AND PRIOR ART

It has long been known that astaxanthin can be prepared from canthaxanthin in low yield via astacin and crustaxanthin. J. Chem. Soc. Chem. Commun. 49 (1967). This process is not suitable for commercial purposes.

From U.S. Pat. No. 4,585,885 it is known that astaxanthin can be prepared in a four-step synthetic sequence from canthaxanthin. The process is indicated to be of commercial value. However, it is apparent that also this process is rather laborious and results in considerable losses and low yields of product.

The reaction sequence as described in U.S. Pat. No. 4,585,885 involves the formation of either an alkylether or a trialkylsilylether as being necessary to protect the initially-formed metal enolate from destruction during the following oxidation reaction which involves the application of an acidic oxidant.

It has recently been described (J. Org. Chem. 49, 3241-3243 (1984)) that trans-2-(phenylsulfonyl)-3-phenyloxaziridine can oxidize certain metal enolates. This oxidizing agent is also known to epoxidize alkene double bonds. Tetrahedron Letters, page 917 (1981).

It is also a well-known fact that carotenoid compounds are extremely sensitive to oxygen and other oxidizing agents, the result being a variety of products rather than any single desired end product. Accordingly, until the present invention, it was not known what effect such an oxidizing agent might have upon the extremely sensitive carotenoid compounds, and especially upon a canthaxanthin compound, particularly a canthaxanthin dienolate, which is employed as a preferred intermediate according to the method of the present invention.

It has now surprisingly been found that astaxanthin can be prepared in a very simple and selective way from canthaxanthin by oxidizing a metal dienolate, a dienamine, or dienolether of canthaxanthin with an oxaziridine oxidant.

The best known method for the production of astaxanthin up until the time of the present invention appears to be that of U.S. Pat. No. 4,585,885, issued Apr. 29, 1986, which produces astaxanthin by a reaction sequence involving four (4) steps, namely, preparation of a lithium enolate, preparation of an alkylsilyl enolether from the lithium enolate, oxidation of the alkylsilyl enolether using a percarboxylic acid, and finally removal of the protecting alkylsilyl groups by hydrolysis. The process of the present invention involves entirely different intermediates than the previous process and does not involve the employment of an alkylsilyl protecting group and removal thereof, consequently shortening the process by the elimination of two (2) steps, thereby rendering the present process more economically efficient, especially since it is conveniently conducted as a single-pot reaction. Moreover, the oxidant employed in the process of the present invention, upon completion of the reaction, is in the form of a compound which is in fact a one-step removed starting material for preparation of the oxidant itself, thereby providing the opportunity for even greater economy by simply recycling the conversion product of the oxidant employed back to produce additional starting oxidant.

OBJECTS OF THE INVENTION

It is an object of the present invention to provide a novel method for preparing astaxanthin from canthaxanthin wherein the enolate of canthaxanthin or other starting canthaxanthin derivative is oxidized without the use of protective groups, as well as to provide key intermediates in said process. Additional objects will be obvious to one skilled in the art and still others will become apparent as the description proceeds.

SUMMARY OF THE INVENTION

In detail, the invention, then, comprises inter alia the following, singly or in combination:

A process for the preparation of astaxanthin having the formula

consisting essentially of the step of decomposing an astaxanthin dihemiaminal having the formula

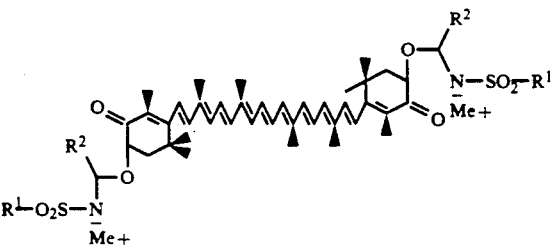

wherein $R^1$ is phenyl, phenyl substituted with a substituent which is stable under the conditions of reaction, $C_{3-7}$-cycloalkyl, camphoryl, or another cyclic or bicyclic radical which may carry alkyl, keto, or other substituents which are stable under the conditions of reaction, and wherein $R^2$ independently signifies hydrogen or the same radical as $R^1$, or wherein $R^1$ and $R^2$ together form a cyclic or bicyclic radical; such a process wherein both $R^1$ and $R^2$ are phenyl; such a
process wherein the astaxanthin dihemiaminal is prepared by oxidation of a canthaxanthin alkali metal dienolate, with a compound having the formula

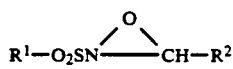

wherein $R^1$ is phenyl, phenyl substituted with a substituent which is stable under the conditions of reaction, $C_{3-7}$-cycloalkyl, camphoryl, or another cyclic or bicyclic radical which may carry alkyl, keto, or other substituents which are stable under the conditions of reaction, and wherein $R^2$ independently signifies hydrogen or the same radical as $R^1$, or wherein $R^1$ and $R^2$ together form a cyclic or bicyclic radical; such a process wherein the astaxanthin dihemiaminal is prepared by oxidation of a canthaxanthin alkali metal dienolate, with a compound having the formula

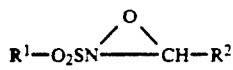

wherein both $R^1$ and $R^2$ are phenyl or wherein $R^1$ and $R^2$ together are camphoryl.

Moreover, an astaxanthin dihemiaminal having the formula

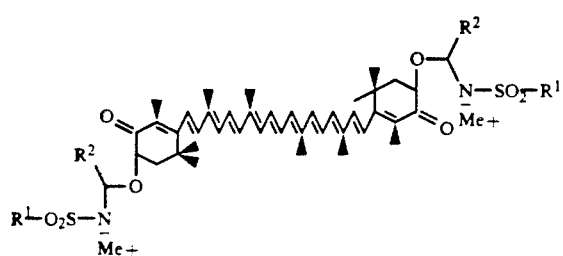

wherein $R^1$ is phenyl, substituted phenyl, $C_{3-7}$-cycloalkyl, camphoryl, another cyclic or bicyclic radical which may carry alkyl, keto, or other substituents, and wherein $R^2$ independently signifies hydrogen or the same radical as $R^1$, or wherein $R^1$ and $R^2$ together form a cyclic or bicyclic radical; such a compound wherein both $R^1$ and $R^2$ are phenyl or wherein $R^1$ and $R^2$ together are camphoryl; such a compound in an organic solvent; and such a composition wherein the solvent is tetrahydrofuran, dioxane, or an aromatic solvent.

Further, such a process wherein the oxidation is carried out in the presence of an organic solvent which is nonreactive with the reactants and reaction products under the conditions of reaction; such a process wherein the solvent is tetrahydrofuran, dioxane, or an aromatic solvent; such a process wherein the oxidation is carried out at a temperature between about −78° C. and −20° C.; such a process wherein the oxidation is carried out in an inert atmosphere; such a process wherein the decomposition is carried out with a proton donor at a temperature up to about 30° C.; such a process which is carried out in the presence of an organic solvent which is non-reactive with the reactants and reaction products under the conditions of reaction and at a temperature up to about 30° C. and employing a proton donor; such a process wherein the proton donor is acetic acid or ammonium chloride; such a process wherein the decomposition is carried out in the presence of an organic solvent which is non-reactive with the reactants and reaction products under the conditions of reaction at a temperature up to about 30° C. and in the presence of a proton donor, and wherein the oxidation is carried out in the presence of an inert gas at a temperature between about −78° C. and −20° C. and in the presence of an organic solvent which is non-recactive with the reactants and reaction products under the conditions of reaction, and finally, such a process wherein an excess of the oxidant is employed.

THE INVENTION

As already stated, according to the process provided by the present invention, astaxanthin is accessible in fewer steps from canthaxanthin than known before, e.g., in U.S. Pat. No. 4,585,885.

The following scheme illustrates the novel process of the invention, which is conveniently carried out as a one-pot reaction:

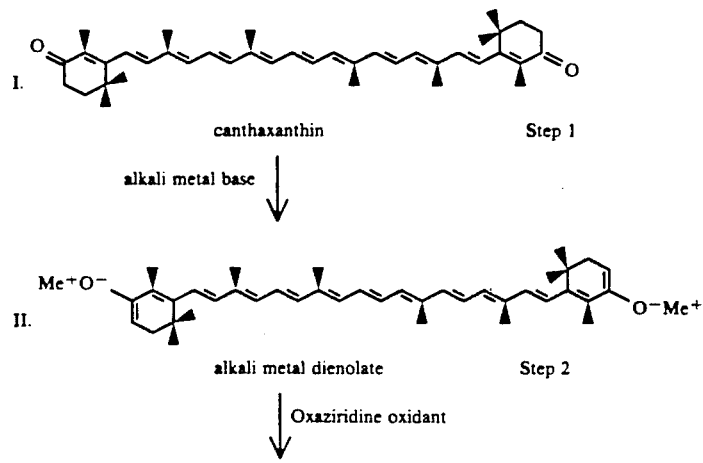

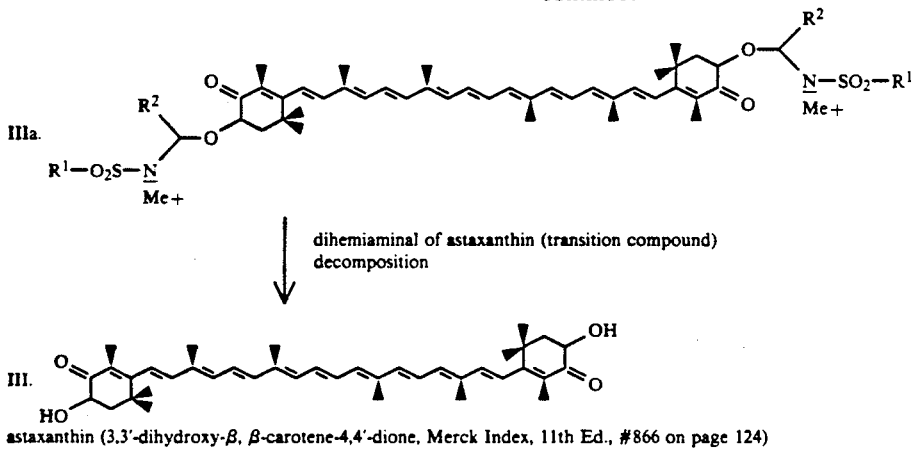

astaxanthin (3,3'-dihydroxy-β, β-carotene-4,4'-dione, Merck Index, 11th Ed., #866 on page 124)

wherein $R^1$ and $R^2$ are as defined hereinafter.

The reactions of the invention as illustrated above are carried out in an organic solvent, which is not critical. Preferred organic solvents or mixtures thereof are selected from ethers, especially cyclic ethers such as for example tetrahydrofuran (THF) and dioxane, aromatic solvents such as for example benzene, toluene and xylene. Among other suitable solvents glymes and dimethylformamide (DMF) can be mentioned. THF and toluene are especially suitable solvents.

Among preferred alkali metal bases for the preparation of the initially-formed metal enolate in step 1 of the above scheme, lithium diisopropylamide and an alkalimetal bis(trimethylsilyl)amide can be mentioned. Other strong alkalimetal bases can be used instead. For example, sodium hydride, potassium hydride, and potassium t-butanolate are suitable. It has been found that sodium bis(trimethylsilyl)amide is especially suitable for the preparation of a reactive canthaxanthin dialkalimetal enolate in step 1 of the above scheme.

The decomposition step as illustrated in the foregoing scheme is an inevitable consequence following the preparation of the dihemiaminal compound of astaxanthin. The decomposition reaction takes place either as a decomposition of the alkalimetal dihemiaminal itself leading to the astaxanthin dialkalimetal alcoholate (which is then quenched to give astaxanthin) and a sulfonimine or the alkalimetal dihemiaminal is protonated by addition of the quenching agent and then the dihemiaminal decomposes to give astaxanthin.

The quenching agent employed according to the invention can be any proton donor. Therefore any protic compound may be employed. Among protic compounds water, alcohols, and hydrogen-donating acids can be mentioned as representative. It is preferred that the quenching proton donor is at least slightly acidic in order to avoid the formation of strong base during the quenching step.

It is preferred to carry out the preparation of astaxanthin from canthaxanthin as a one-pot reaction.

In a preferred procedure for the preparation of astaxanthin according to the invention, canthaxanthin is dissolved in an organic solvent and the reaction conducted at reduced temperature under an inert atmosphere. For example, when the solvent is THF and the inert atmosphere is nitrogen, the temperature may be from about −78° C. to about −20° C. The alkalimetal base in an organic solvent is then added dropwise to the canthaxanthin solution to prepare the alkalimetal dienolate. Then the selected oxidant in an organic solvent is added directly to the already-prepared mixture of canthaxanthin and alkalimetal base, comprising the alkalimetal dienolate in solution or suspension. After decomposition, the desired astaxanthin can be isolated directly by usual techniques.

In another much preferred procedure for carrying out the method of the present invention, the oxidant and canthaxanthin are mixed in an organic solvent or mixture of organic solvents at a reduced temperature under an inert atmosphere. Thereafter the alkalimetal base in an organic solvent is added incrementally to effect the incremental conversion to the alkalimetal dienolate and its concurrent or simultaneous oxidation to astaxanthin. This method is especially suitable for large-scale manufacture of astaxanthin inasmuch as it avoids precipitation of the intermediate alkalimetal dienolate.

In order to effect the reactions of the invention, it has been found advantageous to employ slight excesses of the alkalimetal base and of the oxidant. For example, it has been found that 1.2 equivalents of the base and 1.3 equivalents of the oxidant give excellent yields of the end product (astaxanthin). Equivalent or near equivalent amounts of base and oxidant will, however, still give satisfactory amounts of the desired end product.

Preferred oxaziridine oxidants, as employed according to the present invention, are known and have the formula

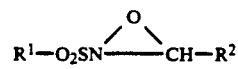

wherein the $R^1$ radical is phenyl, substituted phenyl, e.g., phenyl substituted with halogen, nitro, cyano, $C_{1-4}$-alkyl or $C_{1-4}$-alkoxy; $C_{3-7}$-cycloalkyl; or camphoryl, or another cyclic or bicyclic radical which may carry alkyl, keto, or other substituents, all of which substituents are not critical except that they should be stable under the conditions of reaction, and $R^2$ independently signifies hydrogen or the same radical as $R^1$, or wherein $R^1$ and $R^2$ together form a cyclic or bicyclic radical.

In order to reduce the production costs of astaxanthin when prepared according to the invention, it is preferred to utilize an oxidant as defined above wherein $R^1$ and $R^2$ are both phenyl. This oxidant gives excellent yields of astaxanthin when prepared from canthaxanthin in the manner of the invention.

The high yields and purity of astaxanthin according to the present invention (in Example 1, 71% isolated yield with greater than 95% purity) compare most favorably with the unisolated yields according to the procedure of U.S. Pat. No. 4,585,885 (Column 8) of 67.5% and the isolated yield of 48% astaxanthin of about 90% purity (Column 10, line 19 thereof).

DETAILED DESCRIPTION OF THE INVENTION

The invention will now be described in greater detail with reference to the following examples, which are given by way of illustration only and are not to be construed as limiting.

EXAMPLE 1

2.82 g (5 mmol) canthaxanthin (from Fluka, Basel, Switzerland, used without prior purification) was dissolved in 150 ml absolute tetrahydrofuran and cooled to $-20°$ C. under nitrogen. 12 ml of 1 M (in tetrahydrofuran) solution of sodium-hexamethyl-disilazane (12 mmol) was added over a period of 5 minutes, and the heterogeneous mixture was stirred for 30 minutes and cooled to $-78°$ C. to give the alkalimetal dienolate. A solution of 3.40 g (13 mmol) trans-2-(phenylsulfonyl)-3-phenyloxaziridine in 30 ml of absolute tetrahydrofuran was added within 5 minutes and the mixture was stirred at $-78°$ C. for an additional 30 minutes to give the dihemiaminal of astaxanthin, which probably subsequently decomposes to give a sulphonimine and the astaxanthindienolate anion. The reaction was then quenched by addition of 698 $\mu$l (12.2 mmol) of glacial acetic acid, and was allowed to reach $0°$ C. After evaporation in vacuo at $30°$ C., the crude reaction product was chromatographed on silica gel with methylene chloride/diethyl ether (9:1) as the eluent. The fraction containing astaxanthin was concentrated in vacuo yielding astaxanthin as violet crystals. The astaxanthin was dissolved in a minimum amount of methylene chloride, precipitated with pentane, and 2.12 g (71% based on starting canthaxanthin) of violet crystals were collected by filtration. Purity estimated by TLC [diethyl ether/pentane (2:1)] was greater than 95%; identified by comparison by $^{13}$C-NMR with an, authentic sample of astaxanthin.

EXAMPLE 2

(Oxidation of Alkalimetal Dienolate as Formed in situ)

113 mg (0.2 mmol) canthaxanthin and 157 mg (0.6 mmol) trans-2-(phenylsulfonyl)-3-phenyloxaziridine was dissolved in 10 ml absolute tetrahydrofuran and cooled to $-78°$ C. under nitrogen 600 $\mu$l of a 1 M solution (0.6 mmol) of sodiumhexamethyl-disilazane was added over a period of 20 minutes, and the mixture was stirred for an additional 20 minutes to give the astaxanthin dihemiaminal by oxidation of the canthaxanthin alkalimetal dienolate as it was formed in situ. The reaction mixture was quenched by addition of 46 $\mu$l (0.8 mmol) glacial acetic acid and the yield of astaxanthin was estimated by TLC diethyl ether/pentane (2:1) to be 20% based on starting canthaxanthin.

EXAMPLE 3

(Different Solvent)

565 mg (1 mmol) canthaxanthin was dissolved in 60 ml absolute toluene and cooled to $-10°$ C. under nitrogen. 3 ml of a 1 M (in tetrahydrofuran) solution of sodium-hexamethyldisilazane (3 mmol) was added over a period of 2 minutes, and the heterogeneous mixture was stirred for 60 min and cooled to $-78°$ C. to produce the alkalimetal dienolate. A solution of 800 mg (3 mmol) trans-2-(phenylsulfonyl)-3-phenyloxaziridine in 20 ml of absolute toluene was added within 5 minutes and the mixture was stirred at $-78°$ C. for an additional 30 minutes to produce the astaxanthin dihemiaminal, which probably subsequently decomposes to give a sulphonimine and the astaxanthindienolate anion. The reaction mixture was quenched by addition of 172 $\mu$l (3 mmol) glacial acetic acid, and was allowed to reach $0°$ C. After evaporation in vacuo at $30°$ C., the crude reaction product was chromatographed on silica gel with methylene chloride/-diethyl ether (9:1) as the eluent. The fraction containing astaxanthin was concentrated in vacuo yielding 80 mg (13%) astaxanthin as violet crystals.

EXAMPLE 4

(Different Base and Quenching Agent)

1 g (1.77 mmol) canthaxanthin was dissolved in 20 ml absolute tetrahydrofuran and cooled to $-10°$ C. under nitrogen. 10.6 ml of 0.5 M (in toluene) solution of potassiumhexamethyl-disilazane (5.31 mmol) was added over a period of 5 minutes, and the heterogeneous mixture was stirred for 30 minutes and cooled to $-78°$ C. to prepare the alkalimetal dienolate. A solution of 1.39 g (5.31 mmol) trans-2-(phenylsulfonyl)-3-phenyloxaziridine in 20 ml of absolute tetrahydrofuran was added within 5 minutes and the mixture was stirred at $-78°$ C. for an additional 30 minutes to prepare the astaxanthin dihemiaminal, which probably subsequently decomposes to give a sulphonimine and the astaxanthindienolate anion. The reaction mixture was quenched by addition of 4 ml saturated ammoniumchloride solution and was allowed to reach $0°$ C. The tetrahydrofuran was removed on a rotary evaporator at $30°$ C., 10 ml of water was added, and the mixture was extracted three times with 20 ml methylenechloride. The combined organic phases were washed with 10 ml of brine, dried over sodium sulphate, and concentrated in vacuo at $10°$ C. The crude reaction product was chromatographed on silica gel with methylene chloride/-diethyl ether (9:1) as the eluent. The fractions containing astaxanthin were concentrated in vacuo yielding 82 mg (8%) astaxanthin as violet crystals.

EXAMPLE 5

(Use of Lithium dienolate)

In the same manner as given in Example 1, the process is carried out employing lithium-hexamethyl-disilazane instead of sodium-hexamethyl-disilazane with essentially the same result.

EXAMPLE 6

(Use of Dienolether)

In the same manner as given in Example 5, the lithium dienolate of canthaxanthin is prepared It is then reacted in conventional manner with trimethylchlorosilane to produce the di-(trimethylsilylenolether) of canthaxanthin, which product is then subjected to oxidation in the same manner as given in Example 1 with essentially the same result.

EXAMPLE 7

(Use of Dienamine)

The procedure of Example 6 is repeated, using instead of the trimethylchlorosilane a secondary amine, such as pyrrolidine, piperidine, or dimethylamine, to produce the di(piperidylenamine) or the di(dimethylenamine) of canthaxanthin, which is subjected to oxidation in the same manner as shown in Example 1 with essentially the same result.

EXAMPLE 8

(Different Oxidizing Agent)

In the same manner as given in Example 1, the process is repeated, only using instead of the trans-2-(phenylsulfonyl)-3-phenyloxaziridine the bicyclic oxidizing agent (+)-(2R,8aS)-camphorylsulfonyloxaziridine. The result is essentially the same as in Example 1.

EXAMPLE 9

(Different Solvent)

The procedure of Example 1 is repeated exactly with the exception of the fact that dioxane is substituted as solvent for the tetrahydrofuran. The results are essentially the same as given in Example 1.

EXAMPLE 10

Canthaxanthin bis(trimethylsilyl)-enolether a) A solution of 2.82 g (5 mmol) canthaxanthin in 150 ml absolute tetrahydrofuran is cooled to −15° C. and 12.5 ml of 1 M (in tetrahydrofuran) solution of sodium-hexamethyl-disilazane (12.5 mmol) is added over 5 minutes. The mixture is stirred for 30 minutes and 1.6 ml (12.5 mmol) trimethylchlorosilane is added. After additional stirring for 30 minutes 200 ml of diethylether is added and the organic phase is washed successively with 100 ml icecooled 20% ammoniumchloride and water. The ether phase is dried and concentrated in vacuo. The crude crystalline product is recrystallized from diethylether/methanol (4:1) yielding 95% pure canthaxanthin bis(trimethylsilyl)enol ether as violet crystals.

Astaxanthin bis(trimethylsilyl)ether b) A solution of 1.35 g (2 mmol) canthaxanthin bis(-trimethylsilyl)enol ether in 50 ml absolute tetrahydrofuran is added 1.2 g (4.5 mmol) trans-2-(phenylsulfonyl)-3-phenyloxaziridine and the reaction mixture is stirred for 3 hours. 10 mg (catalytic amount) p-toluenesulphonic acid is added and the mixture is concentrated in vacuo. The remanescens is taken up in 20 ml methylenechloride and 20 ml water and the water phase is extracted twice with methylenechloride. The combined organic phase are dried and concentrated in vacuo, and the remanescens is subjected to column chromatography petroleums ether/diethylether (2:1) yielding the title compound as violet crystals. Mp 191° C.-195° C.

EXAMPLE 11

Astaxanthin (oxidation using camphoryl-oxaziridine)

1.41 g (2.5 mmol) canthaxanthin was dissolved in 200 ml absolute tetrahydrofuran and cooled to −20°0 C. under argon. 6 ml of 1 M (in tetrahydrofuran) solution of sodiumhexamethyl-disilazane (6 mmol) was added over a period of 5 minutes, and the mixture was stirred for 30 minutes and cooled to −78° C. A solution of 1.5 (6.5 mmol) (+)-(2R,8aS)-10-(camphorylsulfonyl)oxaziridine (prepared as described in Organic Synthesis 69 158-168 (1990)) in 30 ml absolute tetrahydrofuran was added within 5 minutes and the mixture was stirred for an additional 60 minutes. The reaction mixture was quenched by addition of 0.35 ml glacial acetic acid and the mixture was concentrated in vacuo. The remanescens was triturated with 25 ml methanol and left at 4° C. overnight, and the formed crystals were filtered of. The crude product was chromatographed on silica gel with methylene chloride/diethyl ether (9:1) as the eluent. The fractions containing astaxanthin was concentrated in vacuo yielding 0.68 g (46% based on canthaxanthin) astaxanthin as violet crystals. The optical purity of the astaxanthin was determined by HPLC analysis of the (−)camphanic acid esters of astaxanthin as described in Journal of High Resolution Chromatography Chromatography Communications 2, 195-196 (1979), and the isomer distribution was 15% (3S, 3'S), 49% (3S, 3'R) and 36% (3R, 3'R).

It is thus seen that the present invention provides a new and economic process for the production of astaxanthin from canthaxanthin according to procedure which permits the elimination of two (2) steps, that is, by a process which involves two steps less than the best known prior art process, involving the employment of novel intermediates and the application of novel oxidizing agents to the said novel intermediates, resulting in production of the highly desirable astaxanthin product, which is in great demand in the fish industry and in the food industry generally for the coloring of food products, in high yields and purity, thus fulfilling a technological and economic demand for a more efficient and simple process, especially since the process of the present invention is well adapted to and preferably conducted as a one-pot reaction.

It is to be understood that the invention is not to be limited to the exact details of operation, or to the exact methods, procedures, or embodiments shown and described, as obvious modifications and equivalents will be apparent to one skilled in the art, and the invention is therefore to be limited only by the full scope of the appended claims.

I claim:

1. A process for the preparation of astaxanthin having the formula

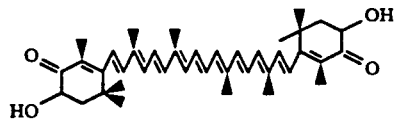

consisting essentially of the step of decomposing an astaxanthin dihemiaminal having the formula

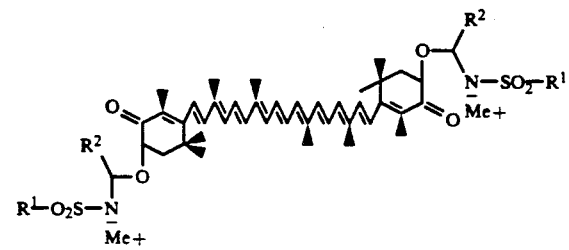

wherein $R^1$ is phenyl, phenyl substituted with a substituent which is stable under the conditions of reaction, $C_{3-7}$-cycloalkyl, camphoryl, or another cyclic or bicyclic radical which may carry alkyl, keto, or other substituents which are stable under the conditions of reaction, and wherein $R^2$ independently signifies hydrogen or the same radical as $R^1$, or wherein $R^1$ and $R^2$ together form a cyclic or bicyclic radical.

2. The process of claim 1, wherein both $R^1$ and $R^2$ are phenyl.

3. The process of claim 1, wherein the astaxanthin dihemiaminal is prepared by oxidation of a canthaxanthin alkali metal dienolate, with a compound having the formula

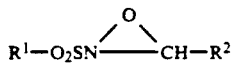

wherein $R^1$ is phenyl, phenyl substituted with a substituent which is stable under the conditions of reaction, $C_{3-7}$-cycloalkyl, camphoryl, or another cyclic or bicyclic radical which may carry alkyl, keto, or other substituents which are stable under the conditions of reaction, and wherein $R^2$ independently signifies hydrogen or the same radical as $R^1$, or wherein $R^1$ and $R^2$ together form a cyclic or bicyclic radical.

4. The process of claim 2, wherein the astaxanthin dihemiaminal is prepared by oxidation of a canthaxanthin alkali metal dienolate, with a compound having the formula

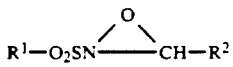

wherein both $R^1$ and $R^2$ are phenyl.

5. The process of claim 1, wherein the astaxanthin dihemiaminal is prepared by oxidation of a canthaxanthin alkali metal dienolate, with a compound having the formula

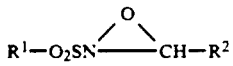

wherein $R^1$ and $R^2$ together are camphoryl.

6. An astaxanthin dihemiaminal having the formula

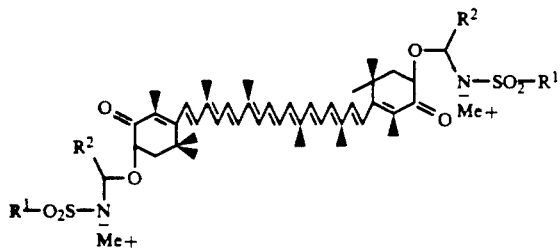

wherein $R^1$ is phenyl, substituted phenyl, $C_{3-7}$-cycloalkyl, camphoryl, another cyclic or bicyclic radical which may carry alkyl, keto, or other substituents, and wherein $R^2$ independently signifies hydrogen or the same radical as $R^1$, or wherein $R^1$ and $R^2$ together form a cyclic or bicyclic radical.

7. A compound of claim 6, wherein both $R^1$ and $R^2$ are phenyl.

8. A compound of claim 6, wherein $R^1$ and $R^2$ together are camphoryl.

9. A compound of claim 6, in an organic solvent.

10. A compound of claim 7, in an organic solvent.

11. A compound of claim 8, in an organic solvent.

12. The composition of claim 9, wherein the solvent is tetrahydrofuran, dioxane, or an aromatic solvent.

13. The composition of claim 10, wherein the solvent is tetrahydrofuran, dioxane, or an aromatic solvent.

14. The composition of claim 11, wherein the solvent is tetrahydrofuran, dioxane, or an aromatic solvent.

15. The process of claim 3, wherein the oxidation is carried out in the presence of an organic solvent which is nonreactive with the reactants and reaction products under the conditions of reaction.

16. The process of claim 15, wherein the solvent is tetrahydrofuran, dioxane, or an aromatic solvent.

17. The process of claim 15, wherein the oxidation is carried out at a temperature between about $-78°$ C. and $-20°$ C.

18. The process of claim 3, wherein the oxidation is carried out in an inert atmosphere.

19. The process of claim 1, wherein decomposition is carried out with a proton-donor at a temperature up to about 30° C.

20. The process of claim 2, which is carried out in the presence of an organic solvent which is non-reactive with the reactants and reaction products under the conditions of reaction and at a temperature up to about 30° C. and employing a proton donor.

21. The process of claim 20, wherein the proton donor is acetic acid or ammonium chloride.

22. The process of claim 4, wherein the decomposition is carried out in the presence of an organic solvent which is non-reactive with the reactants and reaction products under the conditions of reaction at a temperature up to about 30° C. and in the presence of a proton donor, and wherein the oxidation is carried out in the presence of an inert gas at a temperature between about $-78°$ C. and $-20°$ C. and in the presence of an organic solvent which is non-reactive with the reactants and reaction products under the conditions of reaction.

23. The process of claim 5, wherein the decomposition is carried out in the presence of an organic solvent which is non-reactive with the reactants and reaction products under the conditions of reaction at a temperature up to about 30° C. and in the presence of a proton donor, and wherein the oxidation is carried out in the presence of an inert gas at a temperature between about $-78°$ C. and $-20°$ C. and in the presence of an organic solvent which is non-reactive with the reactants and reaction products under the conditions of reaction.

24. The process of claim 3, wherein an excess of the oxidant is employed.

25. The process of claim 24, wherein an excess of the oxidant is employed.

* * * * *

UNITED STATES PATENT AND TRADEMARK OFFICE
CERTIFICATE OF CORRECTION

PATENT NO. : 5,097,063
DATED : March 17, 1992
INVENTOR(S) : Peter Moldt

It is certified that error appears in the above-identified patent and that said Letters Patent is hereby corrected as shown below:

Title Page, [56] References Cited, U.S. PATENT DOCUMENTS,
   line 1, Col. 3; "Sarmatis"      should read -- Surmatis --
   line 5, Col. 1; "4,156,190"    should read -- 4,156,090 --
   line 10, Col. 3; "Bernard et al." should read -- Bernhard et al. --
   line 11, Col. 3; "Bernard et al." should read -- Bernhard et al. --
   (See the original Letters Patents for all of these)

Title Page, [57] ABSTRACT, line 3 (the formula);

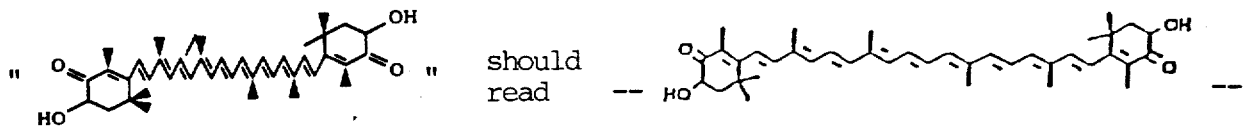

Col. 2, line 33;

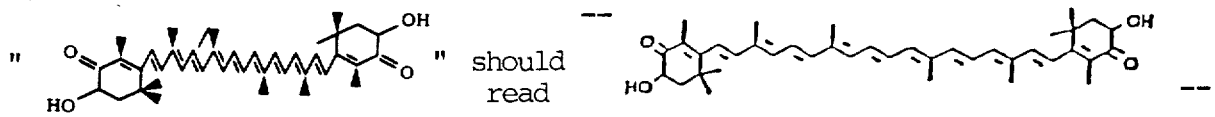

Col. 2, line 45; Col. 3, line 23;                   Col. 10, line 63;
and Col. 11, line 52; change the formula in all four (4) occurrences;

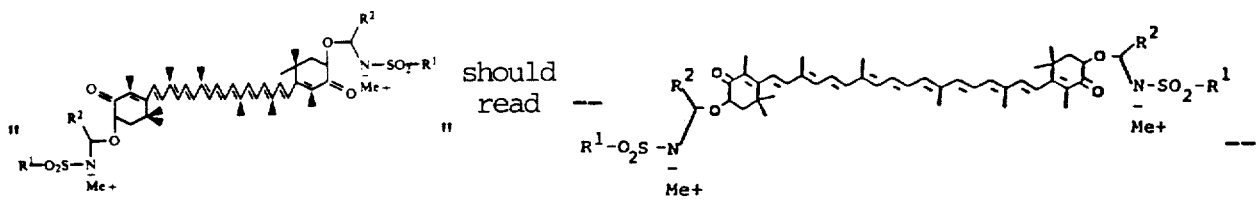

UNITED STATES PATENT AND TRADEMARK OFFICE
CERTIFICATE OF CORRECTION

PATENT NO. : 5,097,063

DATED : March 17, 1992

INVENTOR(S) : Peter Moldt

It is certified that error appears in the above-identified patent and that said Letters Patent is hereby corrected as shown below:

Col. 4, line 29; "recactive" should read -- reactive --

Cols. 3&4, approximately line 52 (second last formula from bottom);

Cols. 3&4, approximately line 62 (last formula);

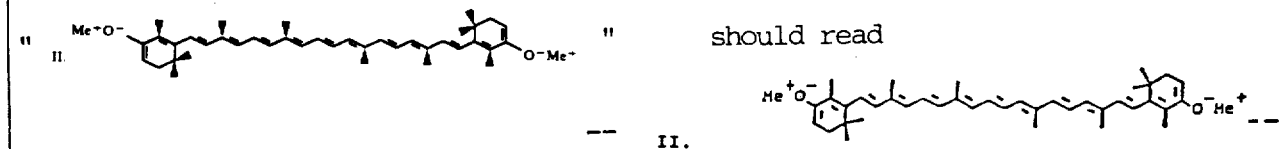

Cols. 5&6, first formula;

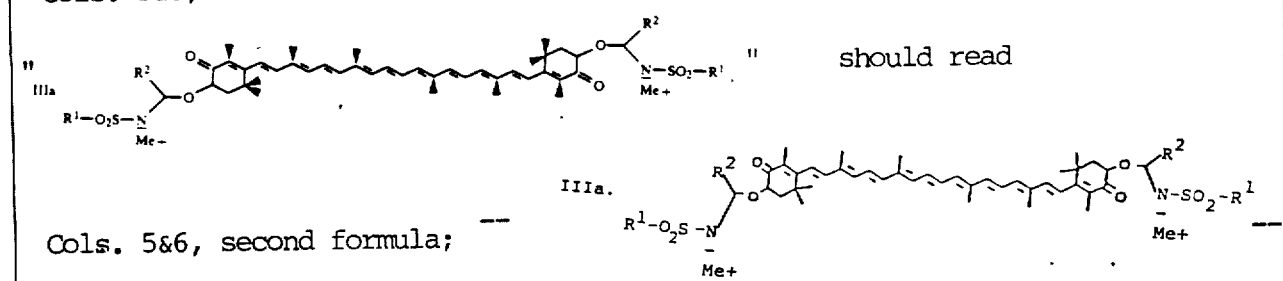

Cols. 5&6, second formula;

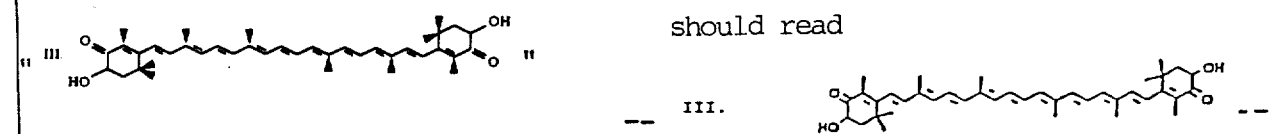

UNITED STATES PATENT AND TRADEMARK OFFICE
CERTIFICATE OF CORRECTION

PATENT NO. : 5,097,063

DATED : March 17, 1992

INVENTOR(S) : Peter Moldt

It is certified that error appears in the above-identified patent and that said Letters Patent is hereby corrected as shown below:

Col. 7, line 52; "nitrogen" should read -- nitrogen. --
Col. 7, line 53; "sodiumhexamethyl-" should read -- sodium-hexamethyl- --
Col. 8, lines 25&26; "potassiumhexamethyl-" should read -- potassium-hexamethyl- --
Col. 8, line 44; "10°" should read -- 30° --
Col. 8, line 46; "chloride/-diethyl" should read -- chloride/diethyl --
Col. 8, line 63; "prepared It" should read -- prepared. It --
Col. 9, line 64; "-20°0 C." should read -- -20° C. --
Col. 9, line 66; "sodiumhexamethyl-" should read -- sodium-hexamethyl- --
Col. 9, line 68; "1.5" should read -- 1.5 g --
Col. 10, line 2; "69" should read -- 69, --
Col. 10, line 9; "of." should read -- off. --
Col. 10, lines 17&18; "Chromatography Chromatography" should read -- Chromatography & Chromatography --
Col. 10, approximately line 52 (the formula);

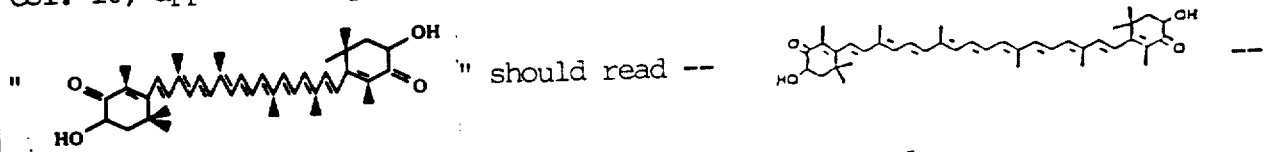 should read --  --

Col. 12, line 29; "proton-donor" should read -- proton donor --

Signed and Sealed this

Sixteenth Day of November, 1993

Attest:

BRUCE LEHMAN

Attesting Officer

Commissioner of Patents and Trademarks